United States Patent [19]
Voris et al.

[11] Patent Number: 5,925,368
[45] Date of Patent: Jul. 20, 1999

[54] PROTECTION OF WOODEN OBJECTS IN DIRECT CONTACT WITH SOIL FROM PEST INVASION

[75] Inventors: Peter Van Voris, Richland, Wash.; W. Eugene Skiens, Wilsonville, Oreg.; Frederick G. Burton, Stansbury Park, Utah; Dominic A. Cataldo, Kennewick, Wash.

[73] Assignee: Battelle Memorial Institute, Richland, Wash.

[21] Appl. No.: 08/484,967

[22] Filed: Jun. 7, 1995

Related U.S. Application Data

[63] Continuation-in-part of application No. 07/402,122, Sep. 1, 1989, abandoned, which is a continuation-in-part of application No. 06/555,113, Nov. 23, 1983, Pat. No. 5,116,414, which is a continuation-in-part of application No. 06/314,809, Oct. 26, 1981, abandoned, and application No. 06/314,810, Oct. 26, 1981, abandoned.

[51] Int. Cl.[6] ................................................. A01N 25/00
[52] U.S. Cl. .................. 424/405; 424/406; 424/407; 424/408; 424/409; 424/412; 424/417; 424/419; 424/421; 424/484; 424/487; 424/DIG. 8
[58] Field of Search ................................... 424/405–409, 424/412–413, 417, 419, 421, 484–487, DIG. 8, 411

[56] References Cited

U.S. PATENT DOCUMENTS

| | | |
|---|---|---|
| Re. 32,356 | 2/1987 | Cordarelli . |
| 1,999,458 | 4/1935 | Hollister . |
| 2,970,404 | 2/1961 | Beaufils et al. . |
| 3,111,403 | 11/1963 | Soper . |
| 3,257,190 | 6/1966 | Soper . |
| 3,367,065 | 2/1968 | Cravens . |
| 3,502,458 | 3/1970 | Schenk . |
| 3,592,792 | 7/1971 | Newland . |
| 3,608,062 | 9/1971 | Krefeld et al. . |
| 3,639,583 | 2/1972 | Cardarelli et al. . |
| 3,671,548 | 6/1972 | Itaya et al. . |

(List continued on next page.)

FOREIGN PATENT DOCUMENTS

| | | |
|---|---|---|
| 48655/90 | 8/1990 | Australia . |
| 62329/90 | 3/1991 | Australia . |
| B-82443/91 | 2/1992 | Australia . |
| B-23427/84 | 8/1994 | Australia . |

(List continued on next page.)

OTHER PUBLICATIONS

Batelle Technology Transfer Bulletin, "Controlled–Release Chemicals for Inhibiting Plant Roots," 2 pgs. (Dec. 1984).
Cline et al., "Biobarriers used in Shallow Burial Ground Stabilization," *Nuclear Technology*, vol. 58, pp. 150–153 (1982).

(List continued on next page.)

*Primary Examiner*—Neil S. Levy
*Attorney, Agent, or Firm*—Arnold White & Durkee

[57] ABSTRACT

A method and device are disclosed which preventing the decay and deterioration of wooden objects caused by pests by using a controlled release device. This controlled release device utilizes polymers which incorporate pesticides. In the disclosed method, the controlled release device is placed in contact with the wood of the wooden object. The pesticide is gradually released from the device and absorbed into the wood structure. The pesticide absorbed by the wood creates a barrier or an exclusion zone to penetration by inserts. The controlled release device maintains a minimal effective level of pesticide in the barrier or exclusion zone for a predetermined period of time.

41 Claims, 7 Drawing Sheets

U.S. PATENT DOCUMENTS

| | | |
|---|---|---|
| 3,691,683 | 9/1972 | Sterzik . |
| 3,705,938 | 12/1972 | Hyman et al. . |
| 3,706,121 | 12/1972 | Jenson . |
| 3,716,560 | 2/1973 | Taya et al. . |
| 3,759,941 | 9/1973 | Sampei et al. . |
| 3,835,176 | 9/1974 | Matsuo et al. . |
| 3,835,220 | 9/1974 | Matsui et al. . |
| 3,846,500 | 11/1974 | Kitamura et al. . |
| 3,851,053 | 11/1974 | Cardarelli et al. . |
| 3,857,934 | 12/1974 | Bernstein et al. . |
| 3,864,114 | 2/1975 | Green . |
| 3,864,388 | 2/1975 | Kitamura et al. . |
| 3,867,542 | 2/1975 | Ueda et al. . |
| 3,876,681 | 4/1975 | Okuno et al. . |
| 3,880,643 | 4/1975 | Cooke et al. . |
| 3,891,423 | 6/1975 | Stanley et al. . |
| 3,899,586 | 8/1975 | Okuno et al. . |
| 3,906,089 | 9/1975 | Okuno et al. . |
| 3,954,814 | 5/1976 | Mizutani et al. . |
| 3,966,963 | 6/1976 | Okuno et al. . |
| 3,970,703 | 7/1976 | Kitamura et al. . |
| 3,981,903 | 9/1976 | Hirano et al. . |
| 3,998,868 | 12/1976 | Mizutani et al. . |
| 4,003,945 | 1/1977 | Kitamura et al. . |
| 4,007,258 | 2/1977 | Cohen et al. . |
| 4,021,122 | 5/1977 | Krenmayr . |
| 4,037,352 | 7/1977 | Hennart et al. . |
| 4,063,919 | 12/1977 | Grano . |
| 4,065,555 | 12/1977 | Potter . |
| 4,077,795 | 3/1978 | Cooke et al. . |
| 4,082,533 | 4/1978 | Wittenbrook . |
| 4,102,991 | 7/1978 | Kydonieus . |
| 4,104,374 | 8/1978 | Reuther et al. . |
| 4,118,505 | 10/1978 | Kitamura et al. . |
| 4,123,250 | 10/1978 | Kupelian . |
| 4,160,335 | 7/1979 | Von Kohorn et al. . |
| 4,172,904 | 10/1979 | Young et al. . |
| 4,176,189 | 11/1979 | Itaya et al. . |
| 4,190,680 | 2/1980 | Young et al. . |
| 4,193,984 | 3/1980 | Kydonieus . |
| 4,198,441 | 4/1980 | Young et al. . |
| 4,198,782 | 4/1980 | Kydonieus et al. . |
| 4,200,664 | 4/1980 | Young et al. . |
| 4,205,096 | 5/1980 | Young et al. . |
| 4,212,879 | 7/1980 | Ohsumi et al. . |
| 4,229,469 | 10/1980 | Mizutani et al. . |
| 4,235,872 | 11/1980 | Tocker . |
| 4,237,113 | 12/1980 | Carderelli . |
| 4,237,114 | 12/1980 | Cardarelli . |
| 4,260,626 | 4/1981 | Carr et al. . |
| 4,263,463 | 4/1981 | Kitamura et al. . |
| 4,269,626 | 5/1981 | Gorke et al. . |
| 4,272,520 | 6/1981 | Kydonieus et al. . |
| 4,279,924 | 7/1981 | Suzuki et al. . |
| 4,282,207 | 8/1981 | Young et al. . |
| 4,282,209 | 8/1981 | Tocker . |
| 4,293,504 | 10/1981 | Suzuki et al. . |
| 4,320,113 | 3/1982 | Kydonieus . |
| 4,327,109 | 4/1982 | Mizutani et al. . |
| 4,334,250 | 6/1982 | Fahlstrom . |
| 4,336,194 | 6/1982 | Ohsumi et al. . |
| 4,344,250 | 8/1982 | Fahlstrom . |
| 4,348,218 | 9/1982 | Bond . |
| 4,350,678 | 9/1982 | Palvarini et al. . |
| 4,352,833 | 10/1982 | Young et al. . |
| 4,360,376 | 11/1982 | Koestler . |
| 4,374,126 | 2/1983 | Cardarelli et al. . |
| 4,376,785 | 3/1983 | Matsuo et al. . |
| 4,377,675 | 3/1983 | Daudt et al. . |
| 4,400,374 | 8/1983 | Cardarelli . |
| 4,405,360 | 9/1983 | Cardarelli . |
| 4,435,383 | 3/1984 | Wysong . |
| 4,457,929 | 7/1984 | Kamachi et al. . |
| 4,496,586 | 1/1985 | Matsui et al. . |
| 4,500,337 | 2/1985 | Young et al. . |
| 4,500,338 | 2/1985 | Young et al. . |
| 4,500,339 | 2/1985 | Young et al. . |
| 4,503,071 | 3/1985 | Hirano et al. . |
| 4,508,568 | 4/1985 | Fox . |
| 4,576,801 | 3/1986 | Parry et al. . |
| 4,579,085 | 4/1986 | McGuire . |
| 4,639,393 | 1/1987 | Von Kohorn et al. . |
| 4,666,706 | 5/1987 | Farquharson et al. . |
| 4,666,767 | 5/1987 | Von Kohorn et al. . |
| 4,680,328 | 7/1987 | Dohrer et al. . |
| 4,747,902 | 5/1988 | Saitoh . |
| 4,767,812 | 8/1988 | Chapin et al. . |
| 4,808,454 | 2/1989 | Saitoh . |
| 4,818,525 | 4/1989 | Kamada et al. . |
| 4,842,860 | 6/1989 | Sugiura et al. . |
| 4,886,656 | 12/1989 | Obayashi et al. . |
| 4,921,703 | 5/1990 | Higuchi et al. . |
| 4,929,497 | 5/1990 | Mitchell et al. . |
| 5,019,998 | 5/1991 | Cowan et al. . |
| 5,104,659 | 4/1992 | Fishbein et al. . |
| 5,116,414 | 5/1992 | Burton et al. . |
| 5,135,744 | 8/1992 | Alexander et al. . |
| 5,139,566 | 8/1992 | Zimmerman . |
| 5,181,952 | 1/1993 | Burton et al. . |
| 5,201,925 | 4/1993 | Itzel et al. . |
| 5,292,504 | 3/1994 | Cardin et al. . |
| 5,296,227 | 3/1994 | Norval et al. . |
| 5,317,834 | 6/1994 | Anderson . |
| 5,439,924 | 8/1995 | Miller . |
| 5,449,250 | 9/1995 | Burton et al. . |
| 5,492,696 | 2/1996 | Price et al. . |

FOREIGN PATENT DOCUMENTS

| | | |
|---|---|---|
| 52454/96 | 12/1996 | Australia . |
| 2070231 | 12/1992 | Canada . |
| 0 286 009 A2 | 10/1988 | European Pat. Off. . |
| 0 594 892 | 5/1994 | European Pat. Off. . |
| 1 929 314 | 8/1988 | Germany . |
| 0039601 | 3/1983 | Japan . |
| 86 1133 | 2/1986 | South Africa . |
| 2018593 | 10/1979 | United Kingdom . |
| 2 098 541 | 11/1982 | United Kingdom . |
| WO 90/14004 | 11/1990 | WIPO . |
| WO 84/0244 | 7/1994 | WIPO . |
| WO 95/18532 | 7/1995 | WIPO . |
| WO 97/47190 | 12/1997 | WIPO . |

OTHER PUBLICATIONS

Hughes, "Controlled Release Technology Inhibits Root Growth," *Controlled Release*, p. 15.

Jury et al., "Behaviour Assessment Model for Trace Organics in Soil: I. Model Description," *J. Environ. Qual.*, vol. 12, No. 4, pp. 558–564 (1983).

Jury et al., "Behaviour Assessment Model for Trace Organics in Soil: III. Application of Screening Model," *J. Environ. Qual.*, vol. 13, No. 4, pp. 573–579 (1984).

Jury et al., "Behaviour Assessment Model for Trace Organics in Soil: IV. Review of Experimental Evidence," *J. Environ. Qual.*, vol. 13, No. 4 (1984).

Roseman et al., "Chapter 18: The Use of Controlled Release Herbicides in Waste Burial Sites," *Controlled Release Delivery Systems* Marcel Dekker, NY (1983).

"Soil Fumigants are Remarkably Effective in Stopping Decay of Wood," *Chemical Week*, p. 39, (Sep. 25, 1974). *Abstract.

Chemical Abstracts, 88:75506v (1978).

Chemical Abstracts, 88:154553(5) p. 1177 (1978).

George Lucas and Roger Rowell, Proceedings from the 13th International Symposium on Controlled Release of Bioactive Materials (Aug. 3–6, 1986) at 75.

Vincent Chang and Asher Ota, *Control of Ant Damage to Polyethylene Tubes Used in Drip Irrigation Systems in Hawaiian Sugarcane Fields*, Proceedings from the XVII Congress of the International Society of Sugar Cane Technologists (Marciano Lopez & Carlos Madrazo eds., Feb. 1–11, 1980).

Burton et al., *A Controlled–Release Herbicide Device for Multiple–Year Control of Roots at Waste Burial Sites*, Journal of Controlled Release, 3:1986.

Solie et al., "Simulation of Trifluralin Diffusion in the Soil," *Transactions of the ASAE*, pp. 1463–1467 (1984).

Steyaart, "Proceedings, Eighty–Second Annual Meeting of the American Wood–Preservers' Association: Address," *Crossties*, vol. 68, No. 3, pp. 45–46 (1987).

Streile, "The Effect of Temperature on Pesticide Phase Partitioning, Trasnport, and Volatilization from Soil," *Abstract of the Dissertation*, (1984), 37 pages.

Van Voris et al., "Long–Term Controlled Release of Herbicides: Root–Growth–Inhibiting Biobarrier Technology," 19 pages.

Soil Fumisantr Chem Weekly Sep. 25, 1974 p. 39.

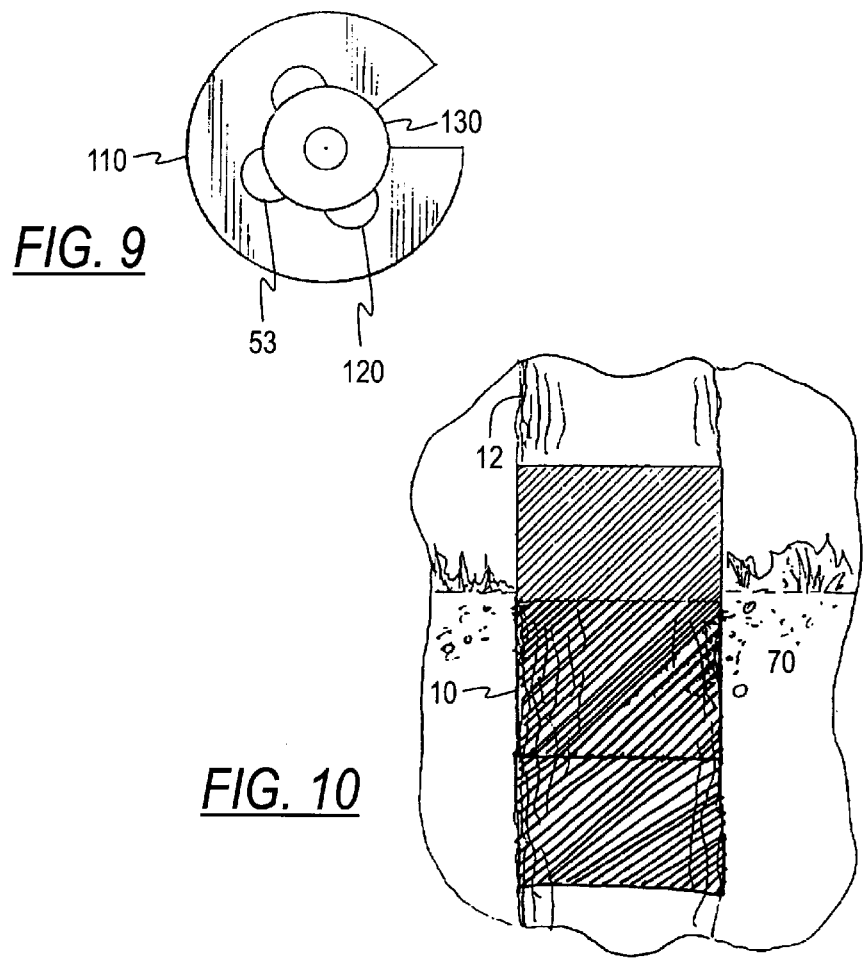
FIG. 9
FIG. 10
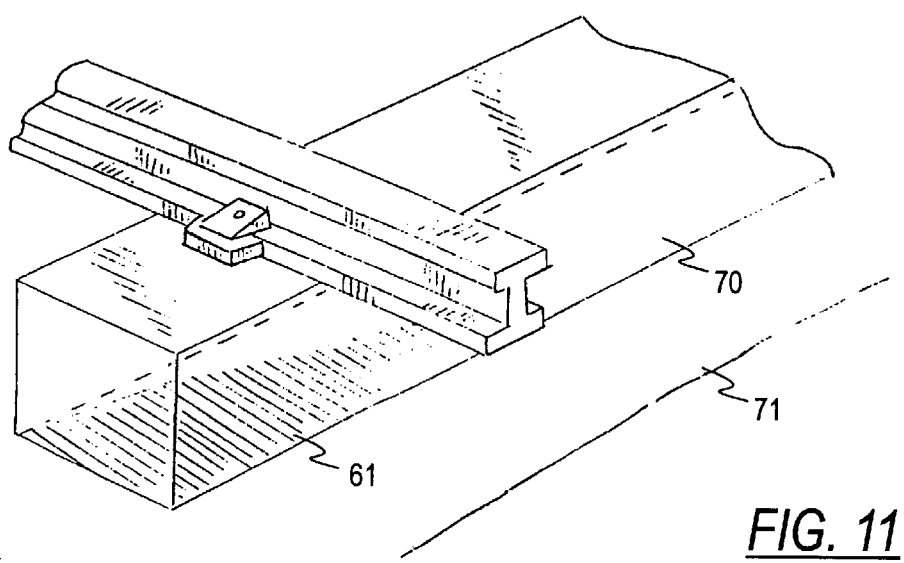
FIG. 11

PROTECTION OF WOODEN OBJECTS IN DIRECT CONTACT WITH SOIL FROM PEST INVASION

CROSS REFERENCE TO RELATED APPLICATIONS

The present application is a Continuation-in-Part of U.S. patent application, Ser. No. 07/402,122 now Abandoned, filed on Sep. 1, 1989, which is a continuation-in-part of U.S. patent application, Ser. No. 555,113 filed on Nov. 23, 1983 now U.S. Pat. No. 5,116,414, which is a continuation-in-part of patent application Ser. Nos. 06/314,809 and 06/314,810, both filed on Oct. 26, 1981, both now Abandoned.

BACKGROUND OF THE INVENTION

This invention pertains to protection of wooden objects in direct contact with soil from pest invasion and is particularly applicable to protection of wooden utility poles, wooden railroad ties and wooden fence posts.

Preserving wood from decay has been recognized as a problem from ancient times. Noah's wooden ark was preserved with pitch (Genesis 6:14). Roman books on architecture had descriptions "of preserving trees after they are cut, what to plaster or anoint them with, of the remedies against their affirmities, and of allotting them their proper place in the building." (See W. C. Hayes, ed., "*Extending Wood Pole Life: Solving a $5-billion/year Problem*", ELECTRICAL WORLD, 41–47 at 42 (February 1986).

In modern times, the protection of wooden utility poles, railroad ties and fence posts from decay has become a major concern. The decay of such wooden objects has been found to be primarily caused by the action of pests and particularly of fungi, termites, carpenter ants, and other wood invading insects.

The decay caused by fungi is a common and an important source of deterioration of wooden objects. (See R. A. Zabel et al., *The Fungal Associates, Detection, and Fumigant Control of Decay in Treated Southern Pine Poles*, Final Report EL-2768 for EPRI Research Project 1471-1, State University of New York 1982). Although decay most frequently occurs within 50 centimeters of the ground line, any part of the pole which has a moisture content of above 20% and is in contact with oxygen can harbor decay-producing fungi. The secondary region of decay is the cross-tie intersection area. The fungi feed on wood by extending networks of minute, thread-like strands of single cells (hyphae) through the cracks in the wood. The hyphae secrete enzymes that dissolve the cellulose and lining in the wood, transforming them into simple chemicals that the fungi then use as food. In its incipient stages, decay is often invisible to the naked eye, but it is capable of completely destroying large volumes of wood. The termites, carpenter ants and other wood invading insects bore into the wood thereby destroying its integrity and structural strength. The problem of invasion by pests is exacerbated by the cracking of wood upon drying. As wood dries to below about 30 percent moisture content, it shrinks. Since the moisture level of freshly-cut wood decreases with the distance form the center, as the wood dries, it produces V-shaped cracks, which expose additional surface for penetration by pests. Additionally, any protection of a wooden object which is limited to the outside surface of such object is rendered inoperative once cracks are formed.

The magnitude of the problem of decay of wood is best illustrated by focusing on wooden utility poles. There are about 120 million wooden utility poles in service in the United States, of which 15 to 20 million are currently in need of treatment to remain in service, and 4 to 6 million more become defective each year. A survey by the Electric Power Research Institute ("EPRI") indicated that, on average, it costs $810 to replace an electric distribution pole, and $1690 to replace an electric transmission pole.

The presently accepted commercial approach to protection of new utility poles involves pressure treatment of the outer layers of the lower portions of poles with various organic or inorganic compounds. A creosote, pentachlorophenol ("penta") arsenicals or fluorides. One widely used preservative is creosote, produced by the destructive distillation of coal. Another organic preservative that has been commonly used to impregnate wooden objects including utility poles is pentachlorophenol ("penta"). However, its use in the United States has been severely restricted by the U.S. Environmental Protection Agency. Wooden poles are also impregnated with inorganic compounds, such as, chromated cooper arsenical (CCA), ammoniacal copper arsenate (ACA) or ammoniacal copper zinc arsenate (ACZA) compounds. A problem with these inorganic wood impregnants, however, is that they leach out and quickly lose their effectiveness in preserving the wood.

A problem common to treatment of wood by impregnation with either organic and inorganic preservatives is that the impregnants reach only the surface layers of the wooden objects. Accordingly, wood cracking exposes untreated areas which are subject to decay.

The pressure impregnation approach provides limited decay protection for a few years up to generally about 15 years. Moreover, the pressure impregnation approach cannot be applied to wooden poles already in place. The decay protection of poles already in place may be extended by periodic inspection and treatment, as necessary, with the fumigants, such as chloropicrin (trichloronitromethane), VAPAM (sodium methyldithiocarbamate) a non-volatile solid which is hydrolyzed to form (methyl isocyanate) or VORLEX a volatile liquid containing the active ingredient of methyl isocyanate in conjunction with physical strengthening of the deteriorated pole. Such remedial treatment has been shown to arrest fungal activity in Douglas fir poles for up to 10 years. (See R. D. Graham et al., *Controlling Biological Deterioration of Wood with Volatile Chemicals*, EPRI Report EL-1480 (Oregon State University, 1980). The treatment with fumigants generally involves drilling a hole at ground level downward and toward the center of the pole and pouring of the fumigant into the hole. The physical strengthening of the deteriorated pole generally lo involves placing reinforcing structures, such as, metal sheath, concrete poured jackets or an adjacent supporting pole.

The problem with the current treatment and repair methods is that they are effective for relatively short periods of time and necessitate regular costly, manpower intensive inspections and continual further treatments and repairs. Providing an excess quantity of an impregnant or a fumigant does not solve the problem of the short duration of the protection. The excess of such impregnant of fumigant is rapidly lost to the air and soil decreasing the long-term effectiveness. Moreover, losses of impregnants or fumigants may cause significant environmental problems. Also, additional impregnants and fumigants are subject to decomposition, which renders them ineffective in the long run and not cost effective in the short run. The concentration of active ingredients resulting from a single application of an impregnant or fumigant starts out well above the minimum level necessary for effectiveness, but decreases rapidly with passing time, dropping quickly below the minimum effective level.

Since a long-term solution to pesticide intrusion is desired, the pesticide which is used to control such intrusion can be incorporated into a controlled release device. A "controlled release device" refers to a substance that results in controlled and sustained release of an active chemical from its surface. The device provides a method for the controlled release of the chemical into the surrounding environment. The chemical released into the environment establishes an effective zone of action.

Presently, there are three controlled release packaging systems including microcapsules, coated granules and chemically-bound fungicides.

While there are a number of reasons for recommending microencapsulation (it is highly versatile, makes use of a variety of manufacturing techniques, and reduces the toxicity of the contained material), it is essentially a short-term system, with lifetimes measured in months rather than years. Additionally, microencapsulation can add significantly to the cost of the fungicide being encapsulated. Furthermore, this process has no use in protecting the other portion of the pole.

The second system involves coated granules. In this case, the fungicide is absorbed onto a matrix such as clay and then coated with cross-linked resins which helps slow the release rate. The presence of relatively large amounts of clay help to reduce the amount of fungicide that can be contained thereby limiting the lifetime of device.

The third system involves chemically-bound fungicides. The fungicide is chemically bound to a polymer either by being reacted with a performed polymer or the fungicide is attached to the monomer and then reacted to form the polymer. As in the case of the coat granules, the lifetime of the system is limited because of the presence of large amounts of polymer which lowers the amount of fungicide that can be contained.

There is, therefore, a long felt and unsatisfied need for a device, a method and a system of preserving wooden objects in contact with soil for a prolonged period of time, by preventing decay and deterioration of such objects by pests such as fungi, termites, ants and other wood invading objects. The need is particularly keen in connection with the prevention of decay and deterioration of wooden utility poles, railroad ties and fence posts.

SUMMARY OF THE INVENTION

The present invention provides a device, and a method for preventing, for a prolonged period of time, the decay and the deterioration of wooden objects in contact with soil caused by the invasion of pests such as fungi, termites, ants and other wood invading insects. The device for releasing any of a variety of pesticidal formulations includes a controlled release device. The controlled release device comprises a polymer matrix which can be selected from one of the four following groups: thermoset polymers, thermoplastic polymers, elastomeric polymers and copolymers thereof. It is preferably inserted inside the wooden object. It can, however, be applied to the outside surface of the object alone or in conjunction with the internally placed device. The controlled-release device releases the pesticide at a predetermined rate to establish a biochemical barrier and maintain the effective concentration of the pesticide in the wooden object to prevent invasion of pests for a predetermined period of time. For devices releasing the pesticide outward from inside of the wooden object, a minimum effective level is maintained throughout the object thereby eliminating problems associated with cracking of the wood. Furthermore, such devices are capable of preventing environmental and health problems caused by the unduly high concentration of the pesticide at the surface of wooden objects or in the local environment around the object.

In accordance with one aspect of the present invention, the device releases pesticide at a high rate initially and a lower, steady rate thereafter. This release profile assures that the wooden object becomes protected in a relatively short period of time and that, subsequent to reaching the minimum effective level only the amount of pesticide necessary to replace the degraded pesticide is released. This release profile diminishes potential environmental and health problems of the treatment and reduces the cost of the treatment.

In accordance with another aspect of the present invention, the device is applied to the outside surface of the wooden object in the form of a coat containing pesticide which is released in a controlled manner. The coat is applied to the external surface of the wooden object and maintains the minimum effective level of pesticide at the surface of the wood and/or in the surrounding soil.

In accordance with another aspect of this invention, a member which at least partially covers the surface outside is externally applied to the wood object. This member with reservoirs holding the controlled release device provides the minimum effective level of pesticide to protect the wood structure.

In accordance with the further object of the present invention, the device is placed inside the wooden object at about ground level allowing the pesticide to be carried laterally and longitudinally by molecular and gaseous diffusion and longitudinally primarily by the capillary action of the wood structure and moisture.

The present invention, together with the attendant objects and advantages, will best be understood with reference to the detailed description below read in conjunction with the accompanying drawings.

BRIEF DESCRIPTION OF THE DRAWINGS

FIG. 9 is a cross-sectional view of a wooden utility pole surrounded by a controlled-release barrier constructed in accordance with an embodiment of the present invention.

FIG. 10 is a perspective view of the bottom of a wooden utility pole covered with a controlled pesticide release layer constructed in accordance with an embodiment of the present invention.

FIG. 11 is a perspective view of a railroad tie whose lower surface is covered with a controlled pesticide release layer constructed in accordance with an embodiment of the present invention.

DETAILED DESCRIPTION OF THE INVENTION

It has been discovered that the decay and deterioration of wooden objects maintained in soil, can be prevented for a prolonged period of time by a controlled release device which releases a pesticide at a predetermined rate into the wooden object to maintain at least a portion of such object above the pesticide concentration that can be tolerated by pesticides. The devices of the present invention can prevent pest infestation of wooden objects up to the expected lifetime of such objects. For example, the devices of the present invention can prevent pest caused decay and deterioration of wooden utility poles for at least seven (7) years.

The process of the present invention for treating wooden objects can be used on any wooden object; however, as a practical matter it is mostly useful in treating wooden objects which are in soil. The wooden objects for which the present invention is especially useful include: wooden utility poles, wooden railroad ties, wooden bridge parts, such as bridge bracings, wooden fence posts and the like. As it should be clear to one skilled in the art, the term "wooden objects" is used herein to refer to objects made of the wood, i.e., out of dead tree trunk and branches. The term "wooden objects" is not intended to refer to live trees.

The device of the present invention can be installed in wooden objects which are already in the soil and in those which have not yet been placed in the soil. The present invention is effective in treating both the wooden objects that have been infested by pests and those which have not yet suffered from pest infestation. After the device of the present invention is installed in the wooden object, it releases the pesticide at a controlled rate into the wood. The device's pesticide-release rate is selected to maintain at least a portion of the wooden object at the minimum effective level. As used in the specification and the appended claims the term "minimum effective level" is defined to be the pesticide level which can be tolerated by pests. In some applications, a creation of an exclusion zone which pests cannot penetrate is sufficient to protect the entire object. The creation of such a zone is advantageous in that less pesticide is required than if such a level was maintained throughout the whole object. Also, it often is much less expensive to install devices for creation of such zone than for treating the entire object. Finally, the creation of a pest barrier zone is advantageous for ecological and human safety reasons. This is because most of the object does not contain a pesticide.

Figure 1:
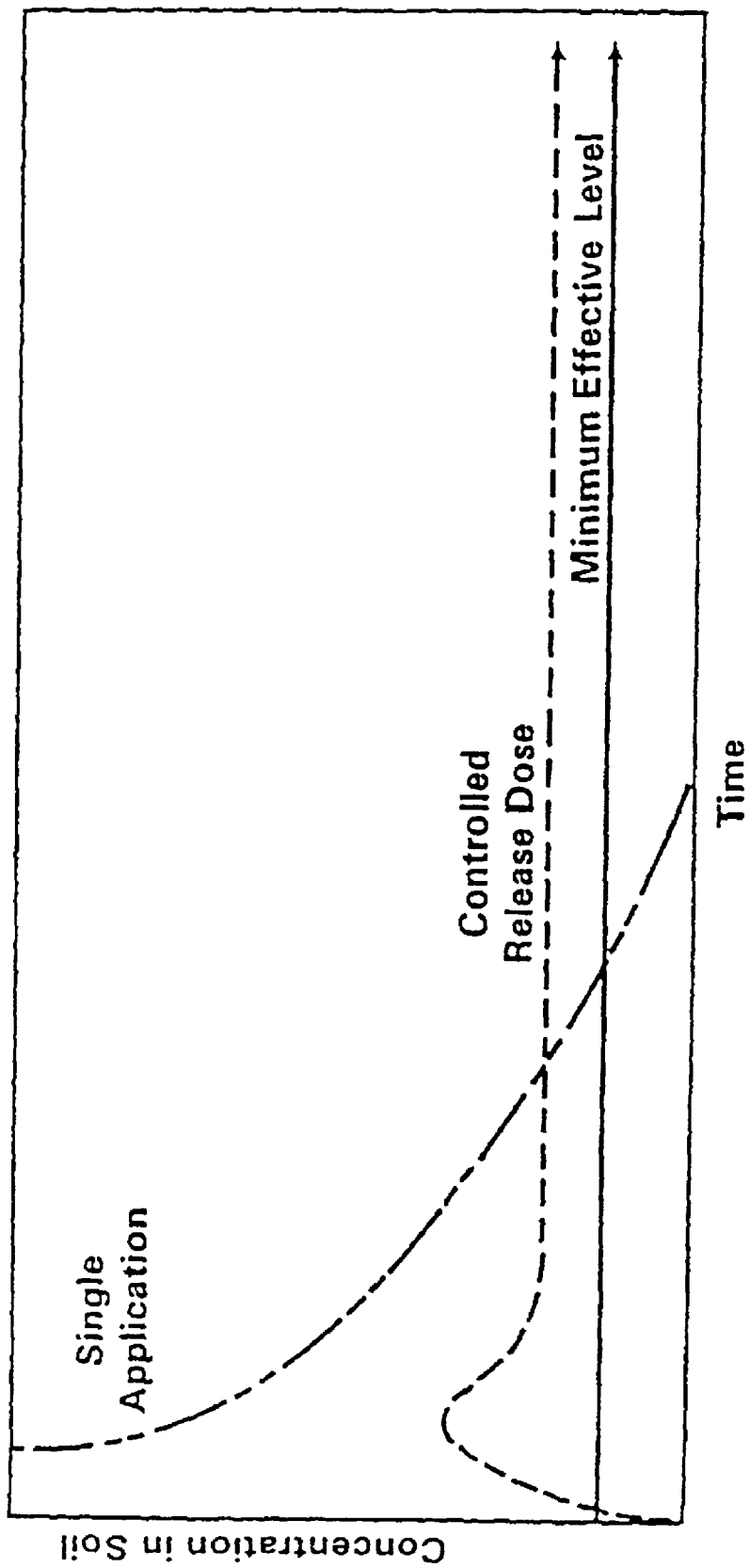
FIG. 1 is a schematic representation of the comparison of concentrations of a pesticide applied in a single dose and by the process and device of the present invention to a wooden object as a function of time.

The controlled release devices of the present invention preferably have a release rate shown in FIG. 1 which is initially rapid so as to bring the pesticide concentration of the zone in the wooden object or the entire object to the desired concentration level as quickly as possible. Thereafter, the release rate is slower, preferably just sufficient to maintain the object or the selected zone of the wooden object above the minimum effective level to prevent pest infestation. The initial high release rate is achieved by allowing the pesticide to release from the matrix prior to inserting the device into or onto the wooden object. The amount of the released pesticide can be varied by the varying temperature and the amount of time for the release prior to inserting the device.

It has been found that polymers serve as effective pesticide release devices because they can act as reservoirs and release regulating mechanisms for the pesticide. They are able to function in this manner because they trap the pesticide within their matrices and matrix acts as a reservoir for the pesticide. Moreover, these polymeric matrices can protect the pesticide from degradation. Thus, the polymeric delivery system is able to maintain an effective dose of the pesticide for a substantial length of time in a zone surrounding the device. A more detailed description of these "controlled release devices" is given in U.S. patent application Ser. Nos. 06/555,113 filed on Nov. 23, 1983 which is a Continuation-in-Part of 06/314,809 and 06/314,810 both filed on Oct. 26, 1981; 07/086,757 filed Aug. 18, 1987, 07/076,080 filed Jul. 10, 1987, and 07/091,918 filed Sep. 1, 1987, the contents of these applications are incorporated herein by reference. Methods for obtaining the release rates are described in patent application Ser. No. 07/303,770 filed on Jan. 30, 1989.

The pesticides used in the present invention depend on the anticipated pests which in turn depend on many factors, including the type of wood, the geographical location of the wooden object and the soil in which the object is maintained. In most cases, the pesticide is selected to eliminate fungi and wood boring insects. The wood boring insects which cause particular problems include carpenter ants and termites (soil born or dry wood). If a single pesticide does not eliminate all of the anticipated pests, the device can incorporate a combination of pesticides, as long as such pesticides are compatible with each other or one another. If the pesticides are not compatible because of different release rates or for other reasons, separate devices can be used for treatment in accordance with the present invention. For termites, the presently preferred pesticide is chlorpyrifos, sold under the trademark Chlorophos by Dow Chemical. Other preferred pesticides include pyrethrins, especially fenoxycarb. Particularly useful as a pesticide in the method and devices of the present invention is tefluthrin. For fungi, the preferred pesticides are tri-chloronitromethane under the tradename chloropicrin, a mixture of methylisothiocyanate and 1,3-dichloropropane under the tradename Vorlex, sodium N-methyl dithiocarbomate under the tradename Vapam. However, 2,3,5,6-tetracholoro-1,9-benzoquinone under the tradename Chloronil and calcium cyanamide can also be used.

Polymer selection for the controlled release device depends upon the conditions encountered either inside the pole or on its outer surface. The polymer matrices must be able to endure the seasonal variations in temperature and moisture. Moreover, because of their naked exposure to the elements, the matrices used to coat the poles must be able to withstand amplified conditions. The polymer utilized in the coating must meet three requirements. First, it must be bound to the wood pole so that it remains intact during handling. Second, it must provide an adequate diffusion barrier for the pesticide so that the release rate will be compatible with the desired service life. Finally, the selection of the polymer must account for the characteristics of the pesticide.

Polymers capable of withstanding such conditions and providing the desired release rates for the pesticides can be classified into four groups: thermoplastic polymers, thermoset polymers, elastomeric polymer and copolymers thereof. By way of example and not intending to limit the scope of this invention, low density polyethylene, high density polyethylene, vinyl acetate, urethane, polyester, silicone, neoprene and disoprene can all be used in this invention.

In addition, it is advantageous to add filler and/or carrier to optimize the loading of the polymer. The inclusion of such a substance allows greater amounts of pesticide to be loaded into the desired polymer while at the same time assisting in the release rate of the polymer. Carbon black is the preferred carrier.

If the controlled release device is inserted into the wooden object, the pesticide must be loaded into the polymer in sufficient amounts to maintain a "minimal effective level." It is preferred to maintain the concentration in parts by weight of the polymer from about 50 to about 80, the concentration of the pesticide from about 10 to about 30, and the concentration of the carrier from about 10 to about 20. By so loading the polymer, the minimum effective level can be maintained for at least seven (7) years. As the concentration profile shown in FIG. 1, a polymeric controlled release device can maintain a minimal effective level of pesticide for much greater periods of time than single application methods.

Figure 4:
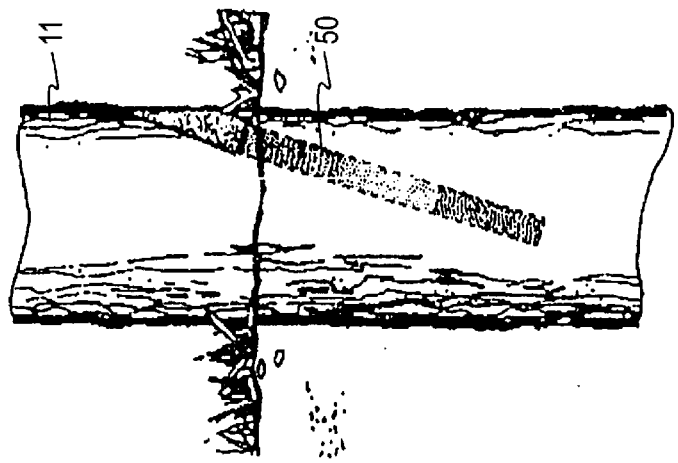
FIG. 4 is a perspective view of the wooden telephone pole of FIG. 3 showing an installed pesticide-releasing device constructed in accordance with the present invention.
Figure 3:
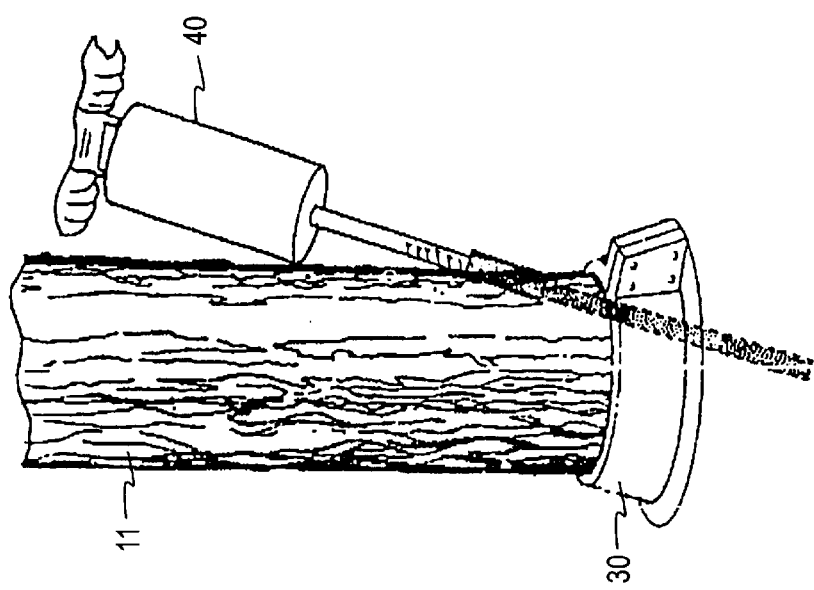
FIG. 3 is a perspective view of a wooden telephone pole being treated by the process of the present invention to install a pesticide-releasing device of the present invention.
Figure 2:
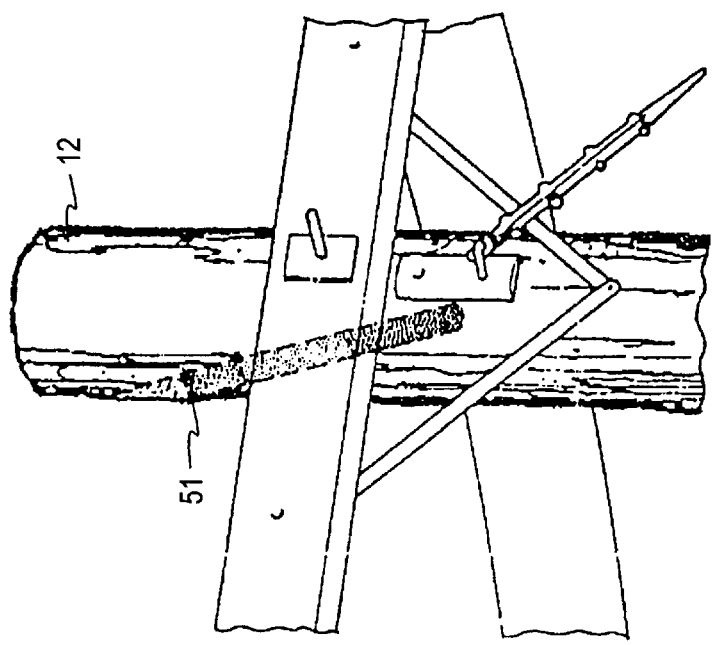
FIG. 2 is a perspective view of a top section of a wooden telephone pole showing the location of the controlled release device constructed in accordance with the present invention.

The devices of the present invention can have any physical shape. If the device is inserted inside the wooden object, it is desirable to have the device shaped to conform to the cavity. Since after the cavity in the wooden objects is best created by drilling a hole therein, the devices of the present invention are often tubular as generally shown in FIGS. 2–4.

In some cases, it is desirable to incorporate the device into the wood in a liquid or in a gel form, which may or may not solidify once it is incorporated. For example, a pesticide can be incorporated into a molten polymer which can then be injected in a molten state into a cavity in the wooden object. The polymer then solidifies creating a solid device which fits tightly in the cavity. Similarly, the pesticide in a molten polymer may be spread on a surface of wooden object and allowed to solidify creating a device which surrounds a portion of the wooden object as illustrated in FIG. 3.

For utility poles as illustrated in FIGS. 2–6, it is preferred to insert the device near the center of the pole so that the pesticide is carried outward by diffusion and longitudinally by the capillary action of the wood structure. Once inserted, the opening into the pole must be sealed (not shown in the drawings). Preferably, the seal utilized provides a diffusion barrier for the pesticide.

Figure 5:
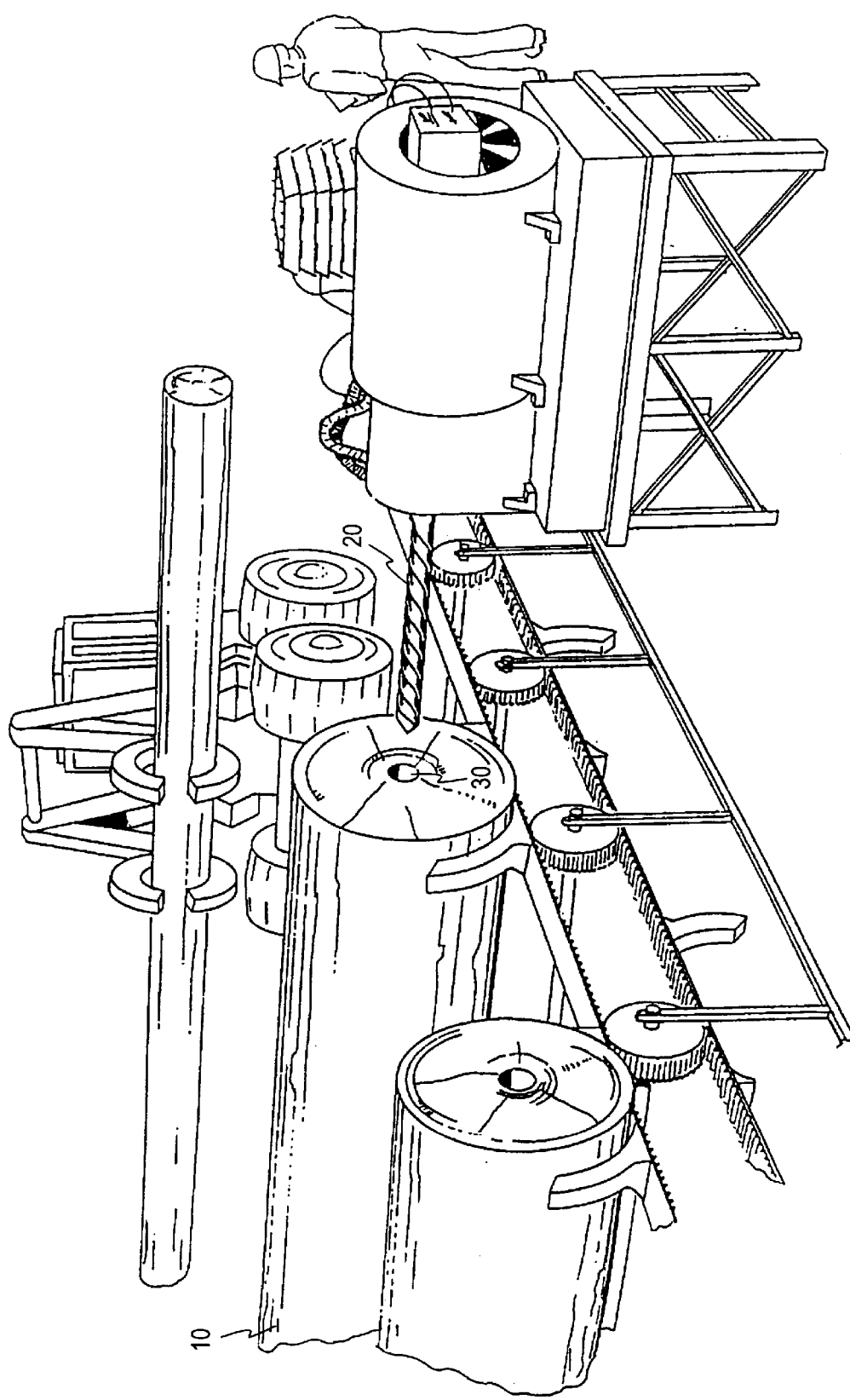
FIG. 5 is a perspective view of drilling operation in the process of installation of the pesticide-releasing device of the present invention into new wooden utility poles.
Figure 6:
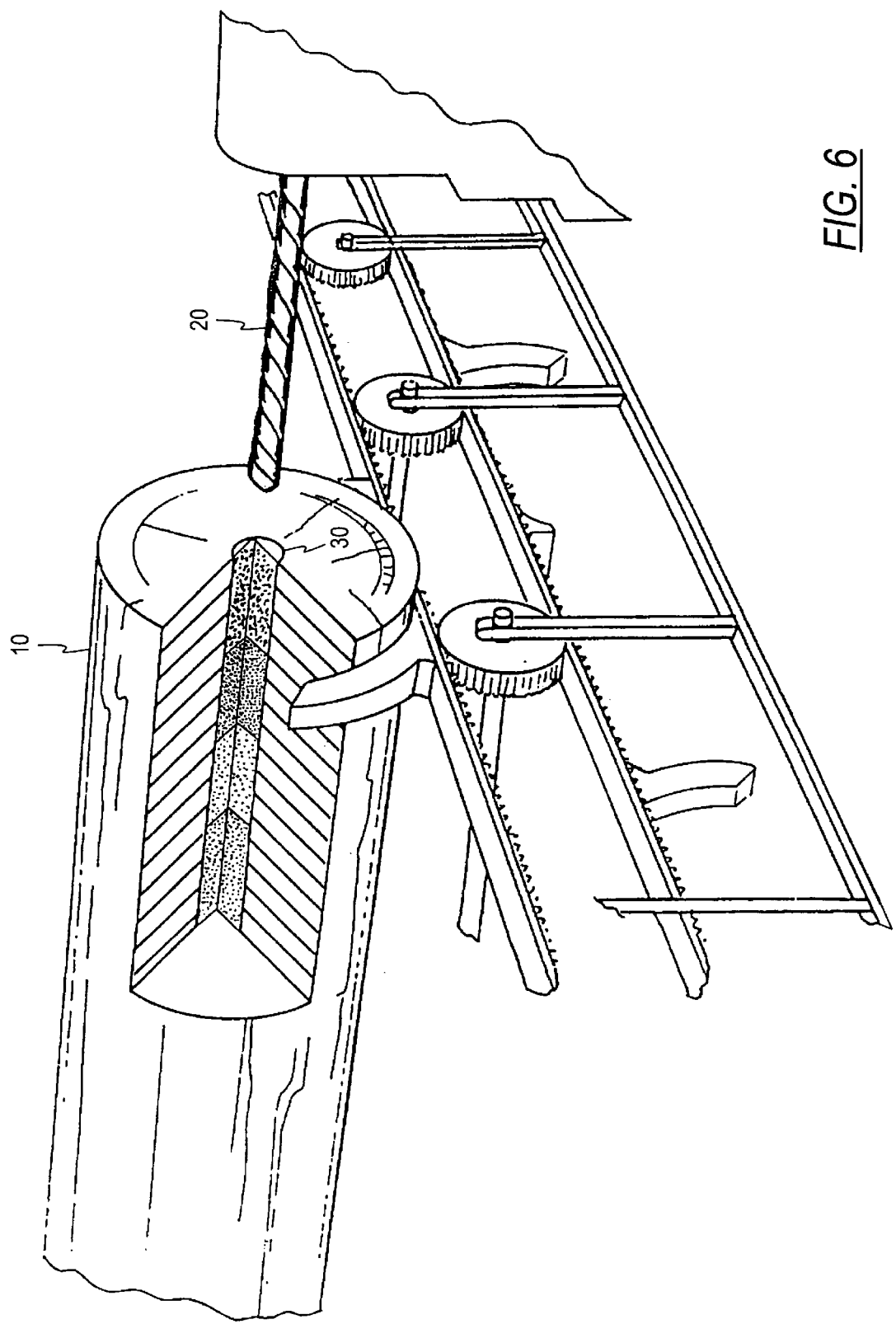
FIG. 6 is a perspective view of the drilling operation of FIG. 5, showing in partial cross-section the bore for the pesticide-releasing device of the present invention.

FIGS. 5 and 6 illustrate the drilling operation of a new utility pole 10. A drill 20 is used to bore a hole 30 in the pole 10 to provide a reservoir for the controlled release device. In distinction, FIG. 3 shows the process of treating an already existing utility pole 11. In this figure, the lower end of the pole 11 is being drilled by a workman using drill 40. A collar 30 is set about the pole 11 to stabilize it as the drill 40 is being pushed downwards into the pole 11. FIG. 4 illustrates the finished pole 11 of FIG. 3 with the controlled release device 50 inserted. FIG. 2 illustrates another embodiment of this invention. It illustrates the controlled release device 51 already inserted near the top of the utility pole 12.

Figure 7:
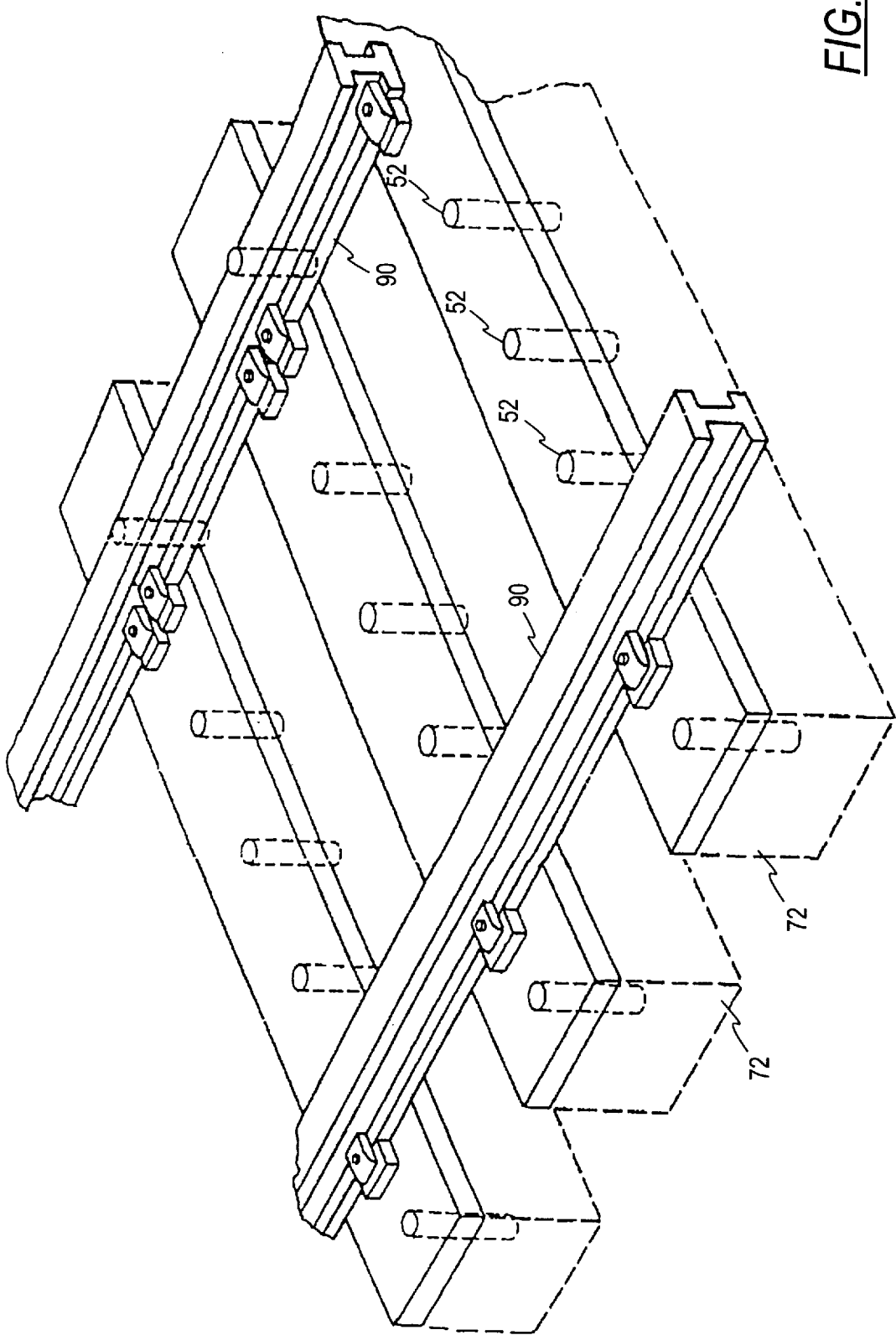
FIG. 7 is a perspective view of the railroad tracks mounted on railroad ties which contain the pesticide-releasing devices constructed and installed in accordance with the present invention.
Figure 8:
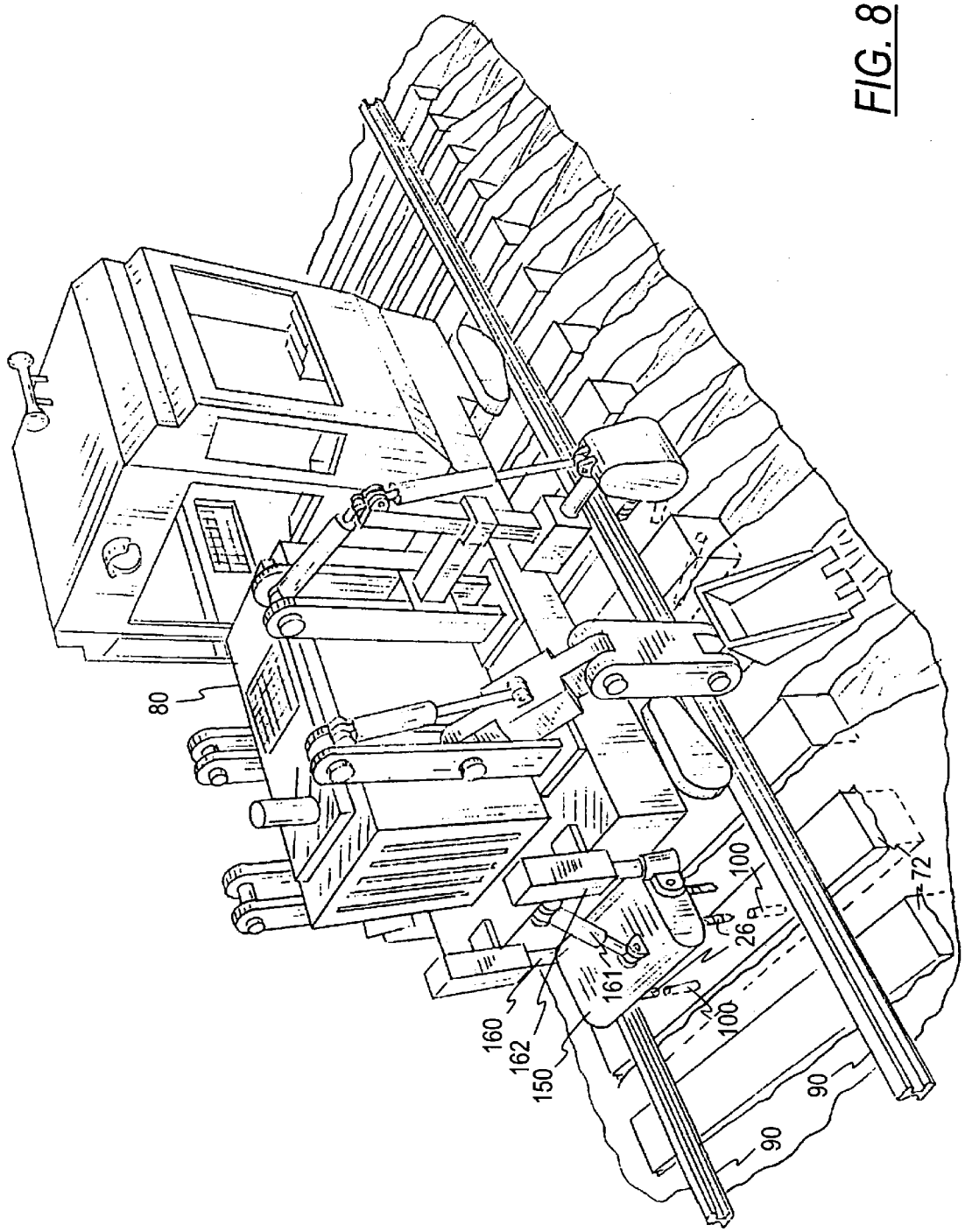
FIG. 8 is a perspective view of a machine for drilling holes in the railroad ties to allow the installation of the pesticide-releasing devices of the present invention.

For railroad cross-ties 72, it is preferred to insert the controlled release device 52 near the center of the tie 72. FIG. 8 illustrates a preferred mode of application. A mechanism 80 which is capable of movement on rails 90 inserts the controlled release device 52 into cross-ties 72. The mechanism 80 utilizes a plurality of drills 22 to bore holes 100 into the cross-ties 72. Member 150 located at the front of the mechanism 80 houses the drills 22. Pistons 160, 161, 162 raise and lower the member 150 so as to allow mechanism 80 to move to the next cross-tie. FIG. 7 shows the finished product. The controlled release devices 52 have been inserted into cross-ties 72.

In another embodiment of this invention, the polymer is placed in contact with the external surface of the wood object. This embodiment provides immediate protection for the wood. The embodiment maintains a minimum effective level of pesticide at the surface of the wood and if in contact with the soil, the surrounding soil. Preferably, the concentration in part by weight of the polymer ranges from about 50 to about 80, the concentration of the pesticide form about 10 to about 30, and the concentration of the carrier from about 10 to about 20. By so loading the polymer, the minimum effective level can be maintained for at least seven (7) years. However, it should be noted that these concentrations can be varied by the user according to the desired results.

FIGS. 10 and 11 describe a mode of providing external contact. A coat 60 is applied to pole 12 in FIG. 10. Similarly, a coat 61 is applied to the bottom of a railroad cross-tie 70. These coats 60, 61 are applied in order to protect the wood structures before the pesticide inserted into the core can diffuse through the wood to reach the outer surface of the wooden object. The coat is able to provide an immediate minimum effective level of pesticide. Depending upon the place of application, this minimum effective level of pesticide can also be instituted in the adjacent soil or structure. Both FIGS. 10 and 11 show the wood (pole 12 or cross-tie 70) being in intimate contact with the surface soil 70 or the cross-ties 71.

In another embodiment for providing external contact, a protective outer layer of pesticide can be applied by using a member 110 with reservoirs 120 to hold the controlled release device 53. The member 110 configured as a ring partially covers the wood object 130. The ring 110, as the applied coating, can be placed on the wood object according to user preference. The coating and ring embodiments of this invention have been shown by way of example and do not limit the scope of this invention.

The pesticide permeates the wooden object by several mechanisms. First, if a polar, water soluble, pesticide is used and the wood contains enough moisture, the pesticide is carried by the capillary action of the wood structure. Second, the pesticide having vapor pressure of above about 1 mm Hg at 25° C. diffuse relatively quickly through the porous molecular wood structure through gaseous diffusion. Such pesticides diffuse through from the center to the periphery of a telephone pole in about 4 to 6 months. The pesticides having vapor pressure equal to or less than about 1 diffuse more slowly than those having vapor pressure of less than about 0.1 mm Hg do not effectively diffuse through the wood.

As stated above, the controlled release device which is applied externally and internally can be placed in a variety of locations. If placed above ground level, the pesticide is carried laterally and longitudinally by molecular and gaseous diffusion and longitudinally by the capillary action of the wood structure and moisture. If placed at or about at ground level, a minimum effective level can also be maintained in the soil or surface surrounding the wood structure. It should be noted that devices made out of polymers containing solid polymeric particles need not include carbon black unless protection from UV degradation is desired or unless carbon black is required to modify the release rate.

EXAMPLE

The following controlled release devices were made and tested to obtain their release rates. The devices were made as follows. All devices, except for those employing S-113 urethane, were injection molded into a thin sheet about ⅛ inch thick. The device employing S113 urethane was cast, a method typically used for thermoset polymers. All thermoplastics were formulated using sufficient amount of carbon black to carry pesticides. All thermoplastic polymers were formulated with 10 percent pesticide, 3 or 7 percent carbon black to absorb liquid pesticide and 87 to 83 percent by weight of polymer. Specifically, devices made from thermoplastic polymers and deltamethrin and lambdacyhalothrin contained 3 percent of carbon black. The devices made from the remaining pesticides and thermoplastic polymers contained 7 percent of carbon black.

The devices made from S-113 urethane (a thermoset polymer) were made from a polymer mix containing 60% S-113, 40% castor oil and 5% of TIPA catalyst by weight. The polymer mix comprised 90% of the total weight of the device. The pesticide, deltamethrin, comprised the remaining 10% of the device. No carbon black was used in this device. The polymer/pesticide mixture was cast, using a spin caster into a ⅛ inch thick sheet and heated at about 60° C. for about 40 to 60 minutes to cure the cast sheet.

One inch squares were then cut from the thin sheets that were injection molded or cast and the squares were tested for release rates. The following release rates were obtained:

| Pesticide | Polymer | Release Rate |
| --- | --- | --- |
| Deltamethrin | S-113 urethane | 25.2 μg/cm2/day |
| | Aromatic 80A | 16.8 μg/cm2/day |
| | pellethane 2102-80A | 8.8 μg/cm2/day |
| | pellethane 2102-55D | 8.0 μg/cm2/day |
| | Alipmtic PS-49-100 | 7.2 μg/cm2/day |
| Cypermethrin | polyurethane 3100 | 0.4 μg/cm2/day |
| | polyurethane 2200 | 0.7 μg/cm2/day |
| | EVA 763 | 27.3 μg/cm2/day |
| | Polyethylene MA7800 | 4.6 μg/cm2/day |
| Lambdacyhalothrin | polyurethane 3100 | 0.7 μg/cm2/day |
| | polyurethane 2200 | 2.0 μg/cm2/day |
| | EVA 763 | 20.6 μg/cm2/day |
| | Polyethylene MA78000 | 5.2 μg/cm2/day |
| Tefluthrin | polyurethane 3100 | 6.4 μg/cm2/day |
| | polyurethane 2200 | 25.0 μg/cm2/day |
| | EVA 763 | 40.4 μg/cm2/day |
| | Polyethylene MA78000 | 27.0 μg/cm2/day |
| Permethrin | polyurethane 3100 | 1.4 μg/cm2/day |
| | polyurethane 2200 | 1.3 μg/cm2/day |
| | EVA 763 | 28.5 μg/cm2/day |
| | Polyethylene MA78000 | 4.0 μg/cm2/day |

It should be apparent that a wide range of changes and modifications can be made to the embodiments described above. It is, therefore, intended that the foregoing description be regarded as illustrative rather than limiting, and that it be understood that it is the following claims, including all equivalents, which are intended to define this invention.

We claim:

1. A method of protecting a wooden object made from dead tree trunks or branches having a porous molecular wood structure, from pests, said method comprising the following steps:
   (a) mixing at least one pesticide, a carrier and a polymer to form a mixture, said polymer being selected from the group consisting of low density polyethylene, high density polyethylene, vinyl acetate, urethane, polyester, silicone, neoprene, disoprene and mixtures thereof, said pesticide being selected from the group consisting of chlorpyrifos, a pyrethrin, fenoxycarb, tefluthrin, trichloronitromethane, a mixture of methylisothiocyanate and 1-3 dichloropropane, sodium N-methyl dithiocarbomate, 2,3,5,6-tetrachloro-1,9-benzoquinone, calcium cyanamide, and mixtures thereof;
   (b) melting the polymer in said mixture to produce a controlled release device, said device comprising a matrix of the polymer, the pesticide and the carrier being trapped within said matrix of the polymer, said at least one pesticide being incorporated into said carrier, said device comprising from about 50 to about 80 parts by weight of said polymer and from about 10 to about 30 parts by weight of the pesticide, the amount of pesticide in said mixture being sufficient to produce a release rate in the range from about 0.4 μg/cm$^2$/day to about 40 μg/cm$^2$/day;
   (c) creating a cavity in the wooden object;
   (d) inserting the controlled release device into the cavity of the wooden object;
   (e) allowing the pesticide from the device to continuously release onto the surface of the device;
   (f) allowing the pesticide to permeate the molecular wood structure of the wooden object so as to create and maintain an exclusion zone within said wooden object, said exclusion zone having a concentration of pesticide above a minimum effective level to prevent pest invasion into said exclusion zone.

2. The method of claim 1 method further comprising the step of permitting the controlled release device to release pesticide onto said surface of the device so that when the device is inserted into the wooden object, the pesticide accumulated on the surface permeates the wooden object initially at a first rate and thereafter at a steady state rate thereafter, the first rate being higher than the steady state rate.

3. The method of claim 1 wherein the exclusion zone having a minimum effective level is created and maintained throughout the whole wooden structure.

4. The method of claim 1 wherein the exclusion zone having a minimum effective level is created and maintained in a portion of the wooden structure.

5. The method of claim 1 wherein the polymer is selected from the group consisting of thermoset polymers, thermoplastic polymers, and elastomeric polymers.

6. A method of protecting a wooden object, made from dead tree trunks or branches and having a porous molecular structure, which had been installed in the soil, from pests, said wooden object having an outside surface, comprising the steps of:
   (a) mixing at least one pesticide, a carrier and a polymer to form a mixture, said polymer being selected from the group consisting of low density polyethylene, high density polyethylene, vinyl acetate, urethane, polyesters silicone, neoprene disoprene and mixtures thereof, said pesticide being selected from the group consisting of chlorpyrifos, a pyrethrin, fenoxycarb, tefluthrin, trichloronitromethane, a mixture of methylisothiocyanate and 1-3 dichloropropane, sodium N-methyl dithiocarbomate, 2,3,5,6-tetrachloro-1,9-benzoquinone, calcium cyanamide, and mixtures thereof;
   (b) melting the polymer in said mixture to produce a controlled release device, said device comprising a matrix of the polymer, the pesticide and the carrier being trapped within said matrix of the polymer, said device comprising from about 50 to about 80 parts by weight of said polymer and from about 10 to about 30 parts by weight of the pesticide, the amount of pesticide in said mixture being sufficient to produce a release rate in the range from about 0.4 μg/cm$^2$/day to about 40 μg/cm$^2$/day;

(c) placing the controlled release device in contact with the outside surface of the wooden object; and (d) allowing the pesticide from the device to continuously migrate onto the surface of the device and to permeate the wooden object so as to create an exclusion zone in said wooden object having a concentration of pesticide above a minimal effective level to prevent pest invasion into said exclusion zone.

7. The method of claim 6 further comprising the step of permitting the controlled release device to release pesticide onto said surface of the device so that when the device is inserted into the wooden object, the pesticide accumulated on the surface permeates the wooden object at a first rate and thereafter at a steady state rate thereafter, the first rate being higher than the steady state rate.

8. The method of claim 6 wherein the exclusion zone having a minimum effective level is created and maintained throughout the whole wooden structure.

9. The method of claim 6 wherein the exclusion zone having a minimum effective level is created and maintained in a portion of the wooden structure.

10. The method of claim 1 wherein the amount of the carrier is from about 10 to about 20 parts by weight.

11. The method of claim 10 wherein the carrier is carbon black.

12. The method of claim 1 wherein at least one pesticide has vapor pressure more than about 1 mm Hg at 25° C.

13. The method of claim 1 wherein the wooden object comprises a utility pole.

14. The method of claim 13 further including the step of closing the cavity after the step of inserting.

15. The method of claim 13 wherein the pole is placed in soil and the cavity is at about the ground level.

16. The method of claim 1 wherein the object is placed in soil and the cavity is at about the ground level.

17. The method of claim 1 wherein the wooden object comprises a bridge.

18. The method of claim 6 wherein the wooden object comprises a utility pole.

19. The method of claim I wherein the wooden object comprises railroad tie.

20. The method of claim 1 wherein the wooden object comprises a fence post.

21. The method of claim 1 wherein at least one pesticide has a vapor pressure above about 1 mm Hg at 25° C.

22. The method of claim 13 wherein the pesticide has a vapor pressure above about 1 mm Hg at 25° C.

23. The method of claim 1 wherein the first rate is achieved by allowing the pesticide to release from the controlled release device prior to inserting the device into the wooden object.

24. The method of claim 1 wherein at least one pesticide is selected to eliminate wood boring insects.

25. The method of claim 1 wherein at least one pesticide is selected to eliminate fungi.

26. The method of claim 1 further comprising incorporating at least one additional pesticide into the polymer matrix, said pesticides being compatible with each other or one another.

27. The method of claim 24 wherein the pesticide is chlorpyrifos.

28. The method of claim 24 wherein the pesticide is a pyrethrin.

29. The method of claim 24 wherein the pesticide is fenoxycarb.

30. The method of claim 24 wherein the pesticide is tefluthrin.

31. The method of claim 25 wherein the pesticide is selected from the group consisting of trichloronitromethane, a mixture of methylisothiocyanate and 1-3 dichloropropane, and sodium N-methyl dithiocarbomate.

32. The method of claim 25 wherein the pesticide is selected from the group consisting of 2,3,5,6-tetrachloro-1, 9-benzo-quinone and calcium cyanamide.

33. The method of claim 1 wherein the polymer is selected from the group consisting of low density polyethylene, high density polyethylene, vinyl acetate, urethane, polyester, silicone, neoprene and disoprene.

34. The method of claim 33 wherein the matrix of the polymer comprises low density polyethylene.

35. The method claim 34 wherein the carrier is carbon black.

36. The method of claim 35 wherein the concentration of the polymer in the controlled release device is from about 50 to about 80, the concentration of the pesticide from about 10 to about 30 and the concentration of the carrier from about 10 to about 20 parts by weight.

37. The method of claim 1 wherein the carrier is carbon black.

38. The method of claim 6 wherein the amount of the carrier is from about 10 to about 20 parts by weight.

39. The method of claim 38 wherein the carrier is carbon black.

40. The method of claim 6 wherein at least one pesticide has vapor pressure more than about 1 mm Hg at 25° C.

41. The method of claim 6 wherein the carrier is carbon black.

* * * * *

UNITED STATES PATENT AND TRADEMARK OFFICE
CERTIFICATE OF CORRECTION

PATENT NO. : 5,925,368
DATED : July 20, 1999
INVENTOR(S) : Van Voris et al.

It is certified that error appears in the above-identified patent and that said Letters Patent is hereby corrected as shown below:

<u>Title page,</u>
Inventor name please replace "Voris et al." with -- Van Voris et al. --.

<u>Column 7,</u>
Line 26, please delete the work "after" found after -- Since --.

Signed and Sealed this

Eighth Day of January, 2002

Attest:

JAMES E. ROGAN
*Attesting Officer*     *Director of the United States Patent and Trademark Office*